US012232758B2

United States Patent
Noyes et al.

(10) Patent No.: US 12,232,758 B2
(45) Date of Patent: Feb. 25, 2025

(54) SINGLE PORTAL, SURGICAL APPARATUS

(71) Applicant: ResnENT, LLC, Bloomington, IL (US)

(72) Inventors: Willard S. Noyes, Bloomington, IL (US); Robert K. Seidl, Hudson, IL (US)

(73) Assignee: RESNENT, LLC, Bloomington, IL (US)

( * ) Notice: Subject to any disclaimer, the term of this patent is extended or adjusted under 35 U.S.C. 154(b) by 9 days.

(21) Appl. No.: 18/210,590

(22) Filed: Jun. 15, 2023

(65) Prior Publication Data

US 2023/0404617 A1 Dec. 21, 2023

Related U.S. Application Data

(60) Provisional application No. 63/352,502, filed on Jun. 15, 2022.

(51) Int. Cl.
*A61B 17/32* (2006.01)
*A61B 17/00* (2006.01)
(Continued)

(52) U.S. Cl.
CPC .............. *A61B 17/32002* (2013.01); *A61B 2017/00115* (2013.01); *A61B 2017/00367* (2013.01);
(Continued)

(58) Field of Classification Search
CPC .............. A61B 17/32002; A61B 90/30; A61B 90/361; A61B 2017/320032;
(Continued)

(56) References Cited

U.S. PATENT DOCUMENTS 6,068,641 A   5/2000  Varsseveld
6,638,289 B1  10/2003 Johnson et al.
(Continued)

FOREIGN PATENT DOCUMENTS

WO   WO 2005/023084   3/2005
WO   WO 2006/026236   3/2006

OTHER PUBLICATIONS

International Search Report and Written Opinion mailed Nov. 28, 2023 for International Application No. PCT/US2023/025479.
Invitation to Pay Additional Fees mailed Sep. 14, 2023 for International Application No. PCT/US2023/025479.

*Primary Examiner* — Sarah A Long
(74) *Attorney, Agent, or Firm* — Sheppard, Mullin, Richter & Hampton LLP

(57) ABSTRACT

Some implementations of the disclosure are directed to single portal surgical systems. In one implementation, an apparatus includes first, second, and third cannulas. Fluid flows through a proximal opening of the first cannula. The second cannula couples within the first cannula such that an outer wall of the second cannula contacts an inner wall of the first cannula. The second cannula includes a first distal opening and a first slot longitudinally extending along the second cannula. Fluid entering the proximal opening flows through the first slot and exits at a distal end of the. The third cannula couples within the second cannula such that an outer wall of the third cannula is in touching relation with an inner wall of the second cannula. The third cannula includes a second distal opening that rotationally interacts with the first distal opening during tissue debridement.

18 Claims, 16 Drawing Sheets

(51) Int. Cl.
   *A61B 17/34* (2006.01)
   *A61B 90/00* (2016.01)
   *A61B 90/30* (2016.01)

(52) U.S. Cl.
   CPC .......... *A61B 2017/0046* (2013.01); *A61B 2017/320032* (2013.01); *A61B 2017/3447* (2013.01); *A61B 90/30* (2016.02); *A61B 90/361* (2016.02); *A61B 2217/005* (2013.01); *A61B 2217/007* (2013.01)

(58) Field of Classification Search
   CPC ...... A61B 2017/3447; A61B 2017/005; A61B 2017/007
   See application file for complete search history.

(56) References Cited

U.S. PATENT DOCUMENTS

| | | | |
|---|---|---|---|
| 8,870,748 B2 | 10/2014 | Kucklick | |
| 10,271,869 B2 | 4/2019 | McGuckin, Jr. | |
| 11,707,190 B1 * | 7/2023 | Truckai | A61B 34/37 |
| | | | 600/102 |
| 2007/0010823 A1 | 1/2007 | Kucklick | |
| 2011/0270293 A1 * | 11/2011 | Malla | A61B 17/32002 |
| | | | 606/180 |
| 2013/0085498 A1 | 4/2013 | Matusaitais et al. | |
| 2015/0196314 A1 * | 7/2015 | Brannon | A61B 17/32002 |
| | | | 606/171 |
| 2018/0214171 A1 | 8/2018 | Ryan, Jr. | |
| 2019/0104932 A1 * | 4/2019 | Truckai | A61B 17/320016 |
| 2021/0100542 A1 * | 4/2021 | Magno | A61B 17/1631 |
| 2024/0099738 A1 * | 3/2024 | Browne | A61B 17/32002 |

* cited by examiner

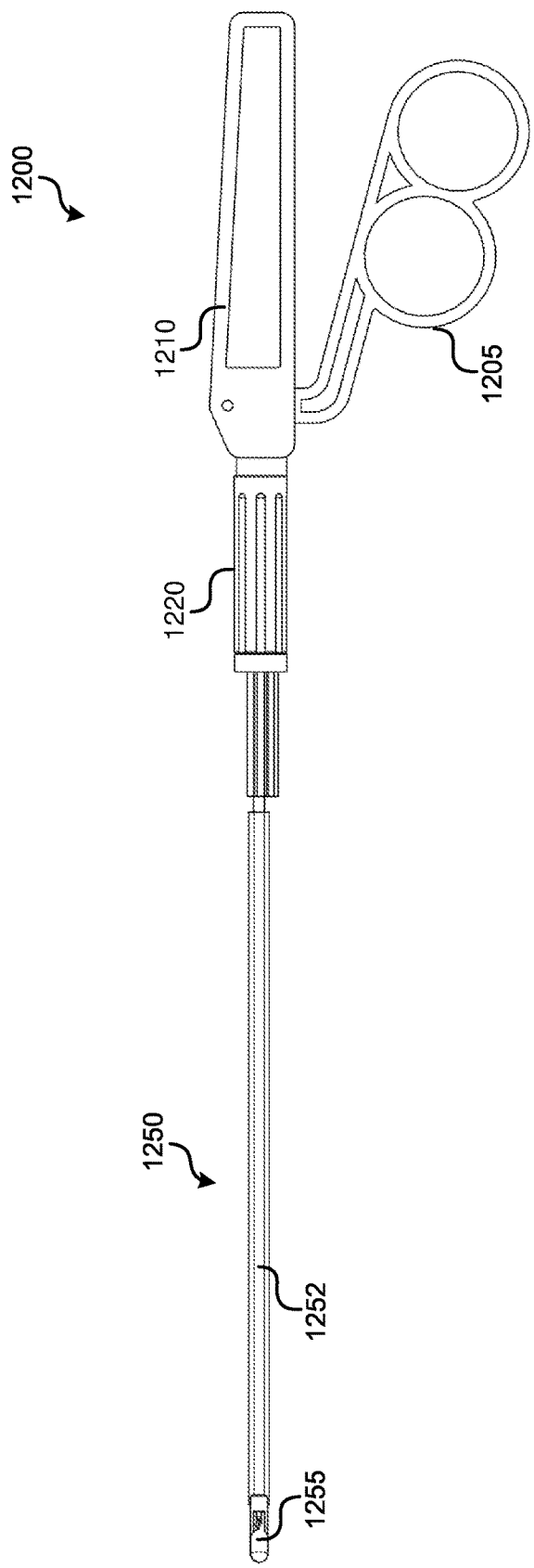
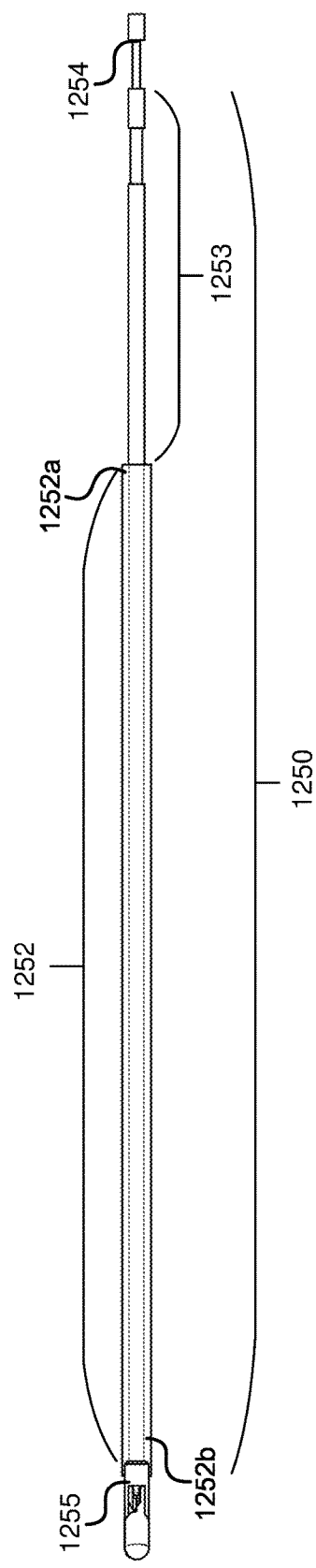
FIG. 12A
FIG. 12B

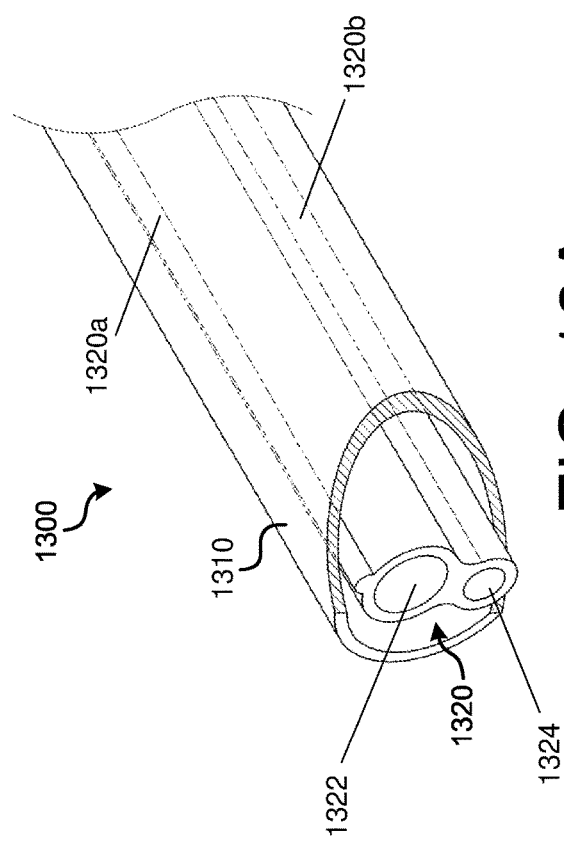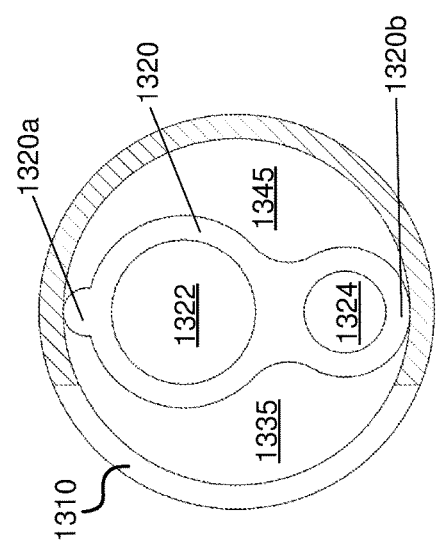

SINGLE PORTAL, SURGICAL APPARATUS

CROSS-REFERENCE TO RELATED APPLICATIONS

This application claims priority to U.S. Provisional Patent Application No. 63/352,502, titled "SINGLE PORTAL, SLOTTED MICRODEBRIDER" filed Jun. 15, 2022, which is incorporated herein by reference in its entirety.

DESCRIPTION OF THE RELATED ART

Orthopedic arthroscopy historically utilizes two or three surgical portals in order to successfully navigate instrumentation within a joint space under endoscopic guidance. One of the more popular instruments used in this regard is a surgical microdebrider. Microdebriders are motorized elongated cannulas that have an inner and outer cannula. The inner cannula rotates or oscillates within the outer cannula. The inner and outer cannula have an opening at the end of the cannula that has sharp or serrated edges. These openings are typically oriented along the side of the cannula tip so that the blunt, rounded tip can protect distal tissue from the cutting action of the microdebrider. In other types of microdebriders a burr is located on the distal tip of the inner shaft that lines up with the side opening of the distal outer cannula tip, again keeping the tip of the cannula protected. Irrigation and suction pumps are often used to regulate the suction and irrigation in a manner adequate to maintain joint space fluid pressure and minimize tissue collapse which would obscure visualization.

SUMMARY

In order for the microdebrider cannulas to work effectually, suction and irrigation must be available in order to prevent tissue, cartilage, and bone from clogging the tip or shaft of the microdebrider cannula. Historically, suction to remove fluid from a joint space is applied either to the back end of the inner microdebrider cannula or via suction ports located on the sides of a separate cannula delivered through a different portal through which an endoscope or microdebrider is placed. In order for there to be enough room for irrigation to flow into the joint space, there needs to be a gap between the outer surface of the endoscope or microdebrider cannula shaft and the inner surface of the outer orthopedic cannula shaft used to gain access to the joint. Eliminating this gap would allow for a smaller overall outer optical cannula diameter.

The arthroscopic surgery market is moving toward smaller endoscopes and instrumentation in an attempt to minimize patient discomfort and allow for in-office arthroscopic procedures. ARTHREX for instance introduced a 1.9 mm "Nanoscope" with a 2.2 mm inflow sheath. These devices however are used for visualization within the joint space. In order to use instruments for tissue removal, a second portal is required to pass instrumentation. The ARTHREX inflow cannula is not large enough to accommodate an endoscope and an instrument such as a forceps or microdebrider cannula within the same inflow cannula.

Performing surgery through a single, optical, orthopedic cannula would be advantageous. A single portal system would minimize the number of incision sites and instrument portals thereby reducing pain and blood loss while at the same time improving surgical speed and efficiency. The smaller the single portal optical cannula diameter, the better tolerated the surgical arthroscopy may be for the patient. On the other hand, in certain applications, a microdebrider shaft should remain as large as possible in order to minimize time necessary for tissue removal. Smaller caliber microdebrider cannulas take longer to debride the tissue. In a single portal system, the optical orthopedic cannula used to gain access to the joint space must provide a large enough inner diameter to allow irrigation, suction, and the passage of a microdebrider shaft or another shafted instrument. If the working channel inner diameter is too small, there would not be enough space to push fluid past the outside of a microdebrider or instrument shaft. In such a situation, standard suctioning through the inner microdebrider cannula would quickly overtake the amount of irrigation flowing into the joint from around the cannula. Similarly, a forceps instrument shaft passed through a single channel optical cannula could only provide one surrounding space between the forceps shaft and inner channel wall for either suction or irrigation to propagate. Suction and irrigation could not occur at the same time through the same cannula.

To address these and other deficiencies of existing or future optical cannula surgical systems, and in an effort to advance a single portal surgical system, implementations of the disclosure are directed to single portal surgical systems and methods, including a slotted microdebrider and customized shaft suitable for single portable surgical applications. Innovating a means by which suction and irrigation can be directed simultaneously through a smaller caliper single optical cannula will minimize the need for multiple instruments inserted through multiple portals into an anatomic space. The technology described herein could be applied to multiple procedures across multiple surgical specialties including orthopedics, otolaryngology, OB/GYN, general surgery, urology, neurosurgery, and veterinary.

In one embodiment, an apparatus comprises: a first cannula to couple to a fluid receptacle such that fluid flows from the fluid receptacle through a proximal opening of the first cannula; a second cannula to couple within the first cannula such that an outer wall of the second cannula is in touching relation with an inner wall of the first cannula, the second cannula including a first distal opening and a first slot longitudinally extending along a length of the second cannula, wherein the fluid entering the proximal opening of the first cannula is to flow through the first slot and exit at a distal end of the apparatus; and a third cannula to couple within the second cannula such that an outer wall of the third cannula is in touching relation with an inner wall of the second cannula, the third cannula including a second distal opening that rotationally interacts with the first distal opening during debridement of tissue. The fluid can exit at a distal end of the apparatus proximal to the first distal opening of the second cannula.

In some implementations, the second cannula further includes a second slot longitudinally extending along the length of the second cannula; and the fluid entering the proximal opening of the first cannula is to flow through the first slot and the second slot, and exit at the distal end of the apparatus.

In some implementations, the second cannula further includes a third slot longitudinally extending along the length of the second cannula; and the first slot, second slot, and third slot are circumferentially spaced along the second cannula.

In some implementations, the fluid entering the proximal opening of the first cannula is to flow through a channel defined by an opening between a first boundary and a second boundary, the opening including the first slot, the first boundary including a longitudinal portion of the inner wall of the first cannula, and the second boundary including a longitudinal portion of the outer wall of the third cannula.

In some implementations, the first slot is substantially linear along the length of the second cannula.

In some implementations, the first slot spirals along the length of the second cannula.

In some implementations, a thickness of the channel is substantially the same as a thickness of the second cannula between the outer wall of the second cannula and the inner wall of the second cannula.

In some implementations, the outer wall of the second cannula is flush against the inner wall of the first cannula along a longitudinal length of the first cannula.

In some implementations, the apparatus further comprises a housing coupled to a proximal end of the third cannula, the housing comprising a port configured to couple to a suction line that suctions the tissue after debridement or the fluid after exiting at the distal end of the apparatus.

In some implementations, an edge of the third cannula along the second distal opening is sharpened.

In some implementations, the apparatus further comprises: a light source to transmit light to a location of the tissue during debridement; and an image sensor to image the location during debridement. In some implementations, the first cannula comprises a light channel via which the light transmitted by the light source travels. In some implementations, the light source is located a distal end of the first cannula (e.g., LED light source), and the light channel is not needed.

In some implementations, the apparatus further comprises the fluid receptacle, and the fluid receptacle is configured to fluidically couple to a fluid source. In some implementations, the fluid receptacle is longitudinally rotatable.

In some implementations, the third cannula is to removably couple within the second cannula.

In some implementations, the third cannula is integrated within the second cannula and/or the second cannula is integrated within the first cannula.

In some implementations, a length of the apparatus is between 5 cm and 25 cm, an outer diameter of the first cannula is between 2.2 mm and 8 mm, and an inner diameter of the third cannula is between 2.0 mm and 7.5 mm.

In one embodiment, an apparatus comprises: a first cannula to couple to a fluid receptacle such that fluid flows from the fluid receptacle through a proximal opening of the first cannula; a second cannula to couple within the first cannula such that an outer wall of the second cannula is in touching relation with an inner wall of the first cannula, the second cannula including a first distal opening and at least one slot longitudinally extending along a length of the second cannula, wherein the fluid entering the proximal opening of the first cannula is to flow through the at least one slot and exit at a distal end of the apparatus; and an instrument shaft to couple within the second cannula such that an outer wall of the instrument shaft is in touching relation with an inner wall of the second cannula. The fluid can exit at a distal end of the apparatus proximal to the first distal opening of the second cannula.

In one embodiment, a single portal surgical apparatus comprises: a first cannula to couple to a fluid source such that fluid flows from the fluid source through a proximal opening of the first cannula; an instrument shaft longitudinally extending within the first cannula, an outer surface of the instrument shaft comprising circumferentially spaced first and second structures longitudinally extending along a distal portion of the instrument shaft, the first structure in continuous, touching relation with a first surface of an inner wall of the first cannula along a first location, and the second structure in continuous, touching relation with a second surface of the inner wall along a second location such that an interior of the first cannula is partitioned into at least two fluid channels having boundaries defined by at least the first location and the second location; and a first tool distally extending from the instrument shaft.

In some implementations, an interior of the instrument shaft comprises a first instrument channel longitudinally extending along the instrument shaft; and the first tool distally extends from a distal end of the first instrument channel.

In some implementations, the single portal apparatus further comprises: a cable wire coupled to the proximal end of the first tool, the cable wire running through the first instrument channel to a proximal end of the single portal surgical apparatus.

In some implementations, the single portal apparatus further comprises: a second tool distally extending from the instrument shaft. In some implementations, an interior of the instrument shaft further comprises a second instrument channel separate from the first instrument channel; and the second tool distally extends from a distal end of the second instrument channel.

In some implementations, the first and second structures circumferentially spiral about the instrument shaft along its longitudinal length.

In some implementations, the first and second structures are winged structures.

In some implementations, the at least two fluid channels comprise a first fluid channel and a second fluid channel; the fluid entering the proximal opening of the first cannula is to flow through the first fluid channel and exit at a distal end of the first cannula; and the second fluid channel is configured to suction the fluid or tissue.

In some implementations, the second fluid channel is coupled to a suction line proximal to the first cannula.

In some implementations, the outer surface of the instrument shaft further comprises a third structure longitudinally extending along the distal portion of the instrument shaft, the third structure in continuous, touching relation with a third surface of the inner wall along a third location, and the third structure circumferentially spaced with the first and second structures; the at least two fluid channels comprise three or more fluid channels; and the interior of the first cannula is partitioned into the three or more fluid channels having boundaries defined by at least the first location, the second location, and the third location.

In some implementations, the single portal surgical apparatus further comprises: a light source to transmit light to an anatomical site during surgery; and an image sensor to image the anatomical site during surgery.

In some implementations, the image sensor is integrated into the first cannula; and the first cannula comprises a channel via which the light transmitted by the light source travels; or a distal end of the first cannula comprises the light source.

In some implementations, the single portal surgical apparatus further comprises: a handle proximal to and coupled to the first cannula and the instrument shaft, the handle comprising a control configured to be actuated to move the first instrument.

In some implementations, the single portal surgical apparatus further comprises: a connector distal to the handle, the connector configured to removably couple a proximal end of the instrument shaft to the handle.

Other features and aspects of the disclosed technology will become apparent from the following detailed description, taken in conjunction with the accompanying drawings, which illustrate, by way of example, the features in accordance with implementations of the disclosed technology. The summary is not intended to limit the scope of any inventions described herein, which are defined by the claims and equivalents.

BRIEF DESCRIPTION OF THE DRAWINGS

The present disclosure, in accordance with one or more implementations, is described in detail with reference to the following figures. The figures are provided for purposes of illustration only and merely depict example implementations. Furthermore, it should be noted that for clarity and ease of illustration, the elements in the figures have not necessarily been drawn to scale.

Some of the figures included herein illustrate various implementations of the disclosed technology from different viewing angles. Although the accompanying descriptive text may refer to such views as "top," "bottom" or "side" views, such references are merely descriptive and do not imply or require that the disclosed technology be implemented or used in a particular spatial orientation unless explicitly stated otherwise.

FIG. 12A shows a single portal surgical apparatus including a winged instrument shaft configured to extend through an outer/optical cannula to divide the inside of the outer/optical cannula into multiple separate channels, in accordance with some implementations of the disclosure.

FIG. 12B shows a side view of the instrument shaft and distal tool of the single portal surgical apparatus of FIG. 12A.

FIG. 13A shows a front perspective view of an assembly of a single portal surgical apparatus, the assembly including an instrument shaft extending through an outer/optical cannula, and in touching relation with an inner wall of the outer cannula, in accordance with some implementations of the disclosure.

FIG. 13B shows a front cross-sectional view of the assembly of FIG. 13A.

The figures are not exhaustive and do not limit the present disclosure to the precise form disclosed.

DETAILED DESCRIPTION

Figure 1A:
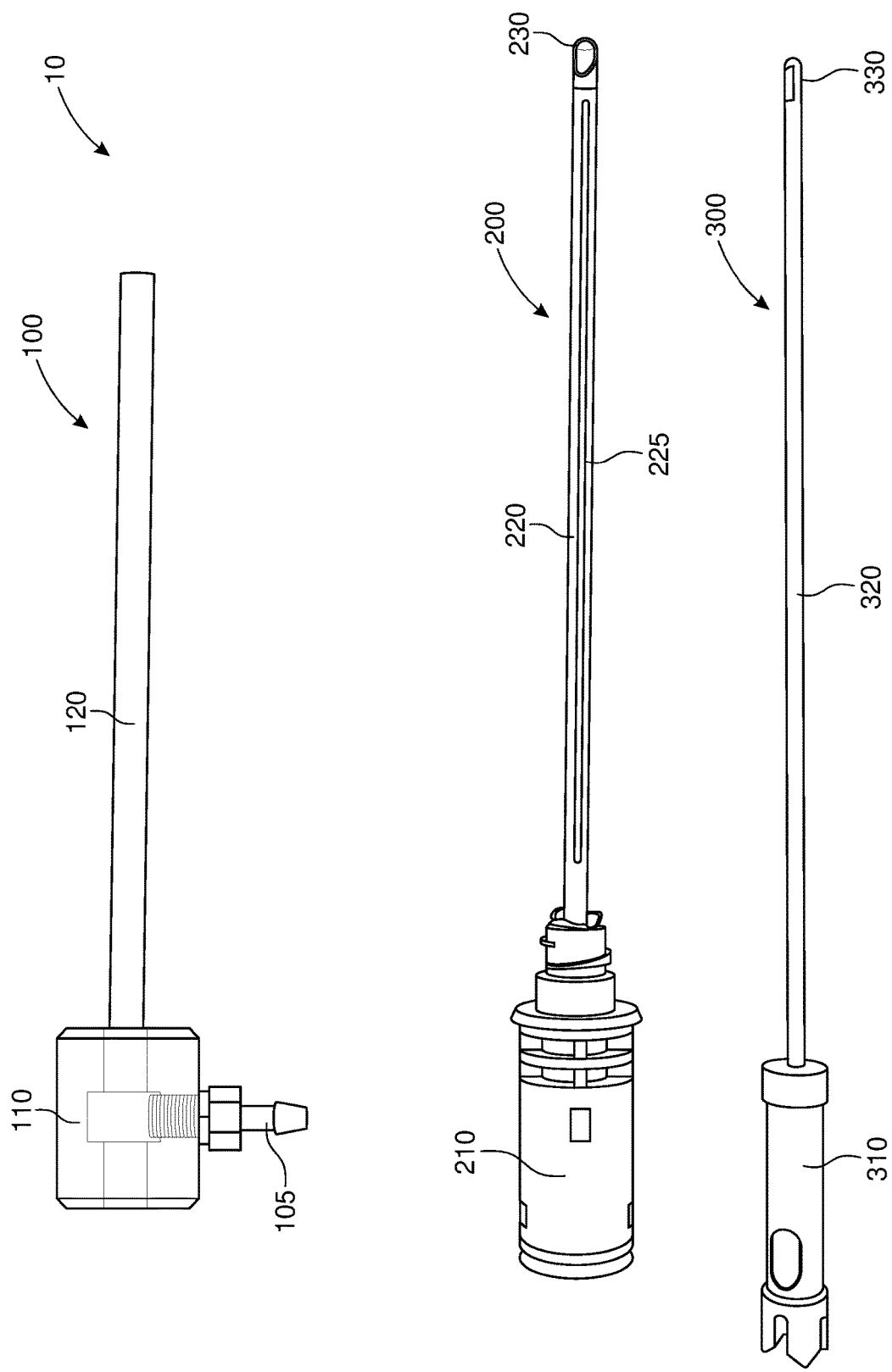
FIG. 1A shows a perspective view of components of a disassembled microdebrider apparatus, in accordance with some implementations of the disclosure.
Figure 1B:
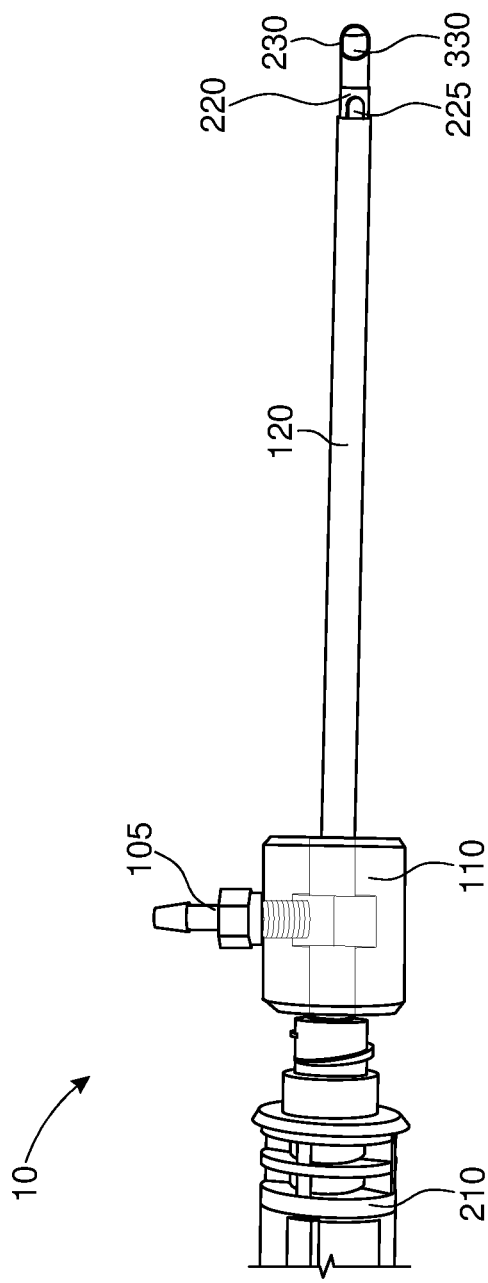
FIG. 1B shows the components of the microdebrider apparatus of FIG. 1A assembled, in accordance with some implementations of the disclosure.

FIGS. 1A-1B depict a single portal microdebrider apparatus 10, in accordance with some implementations of the disclosure. FIG. 1A depicts the disassembled microdebrider apparatus 10, and FIG. 1B depicts the assembled microdebrider apparatus 10. The microdebrider apparatus 10 includes an optical or endoscopic component 100, a microdebrider outer component 200, and a microdebrider inner component 300. As depicted by the example of FIGS. 1A-1B, components 100-300 are all removably coupled, and they may be disassembled. However, depending on the device implementation, all, some, or none of components 100-300 may be disassembled. For example, in one embodiment all of the components are integrated or otherwise combined.

The optical component 100 includes a fluid port 105, a fluid receptacle 110, and a cannula 120. The optical component 100 may also include an endoscopic light source and image sensor (not shown). The light source and/or image sensor may be positioned on a distal end of cannula 120 or in a housing (not shown) at a proximal end of optical component 100. For example, during endoscopic operation of optical component 100, light emitted from a light source (e.g., LED light source) contained within an endoscope housing may transmit light that travels through cannula 120 via an illumination channel that terminates at the distal end of cannula 120. The illumination channel may be a molded illumination pipe. Alternatively, in other implementations the light source may be integrated, internally and/or externally, into the cannula 120. In such implementations, the light source may be positioned near the distal end of cannula 120 (e.g., near the camera sensor, in a different channel such that the light emitted by the light source does not interfere with the operation of the camera sensor), or in some other segment of the cannula 120.

Figure 2:
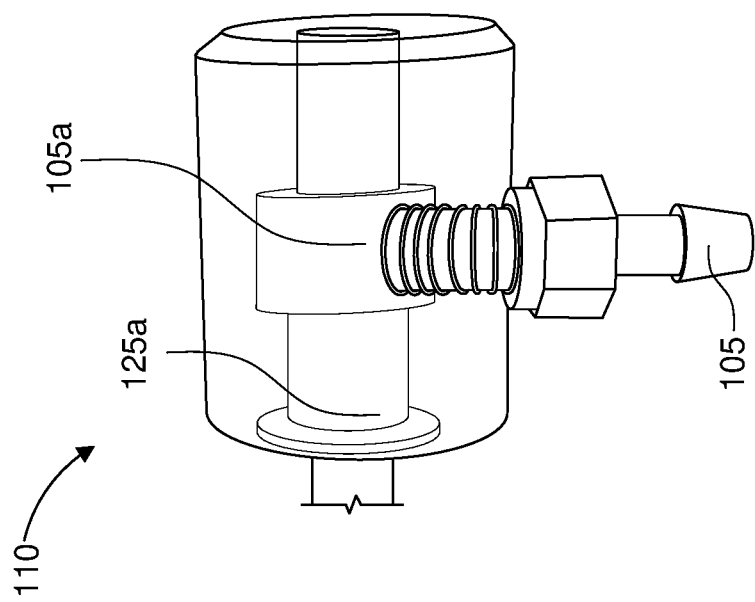
FIG. 2 shows an enlarged view of the fluid receptacle and fluid port of the optical component of the microdebrider apparatus of FIGS. 1A-1B, in accordance with some implementations of the disclosure.
Figure 3A:
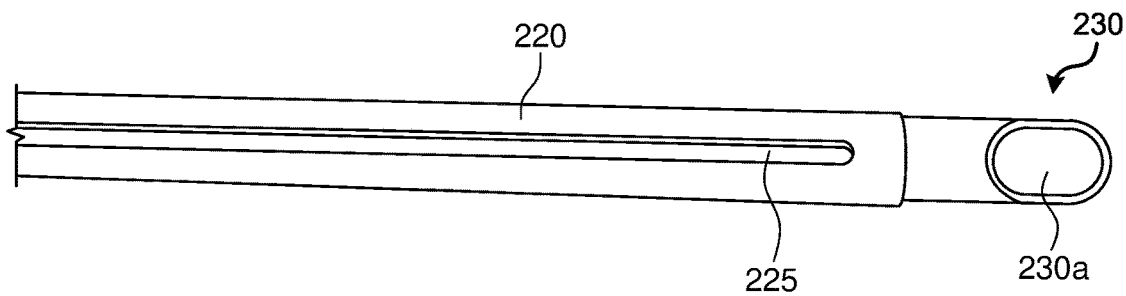
FIG. 3A shows an enlarged view of the cannula and distal end of the microdebrider outer component of the microdebrider apparatus of FIGS. 1A-1B, in accordance with some implementations of the disclosure.
Figure 3B:
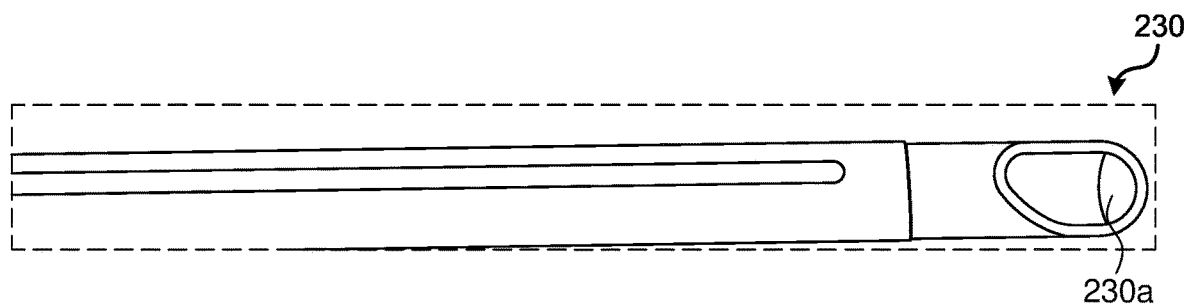
FIG. 3B shows another enlarged view of the cannula and distal end of the microdebrider outer component of the microdebrider apparatus of FIGS. 1A-1B, in accordance with some implementations of the disclosure.
Figure 3C:
FIG. 3C shows another enlarged view of the cannula and distal end of the microdebrider outer component of the microdebrider apparatus of FIGS. 1A-1B, in accordance with some implementations of the disclosure.
Figure 3D:
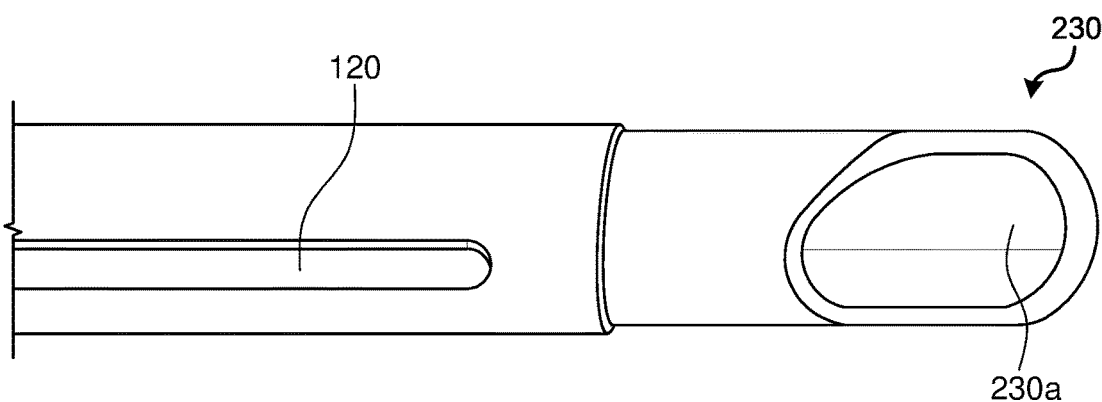
FIG. 3D shows another enlarged view of the cannula and distal end of the microdebrider outer component of the microdebrider apparatus of FIGS. 1A-1B, in accordance with some implementations of the disclosure.

FIG. 2 shows an enlarged view of the fluid receptacle 110 and fluid port 105. As depicted, the fluid port 105 couples to an interior of the fluid receptacle at a junction or channel 105a. Fluid received in channel 105a flows into the cannula 120 at a proximal opening 125a of the cannula 120. In this example, the fluid receptacle 110 may be rotated longitudinally to enable better positioning of a fluid line (not shown) running to fluid port 105, or otherwise improve the ergonomics of the apparatus 10. In some implementations, fluid receptacle 110 can removably couple to optical component 110.

The microdebrider outer component 200 includes head 210, a cannula 220, and distal end or cannula tip 230 that has an opening 230a. FIGS. 3A-3D show various enlarged views of the cannula 220 and distal end 230 of outer component 200, in accordance with some implementations of the disclosure. At least one slot 225 runs longitudinally along the length of cannula 220, which, as further described below, provides a means for delivering fluid to the distal end of apparatus 10.

Figure 4A:
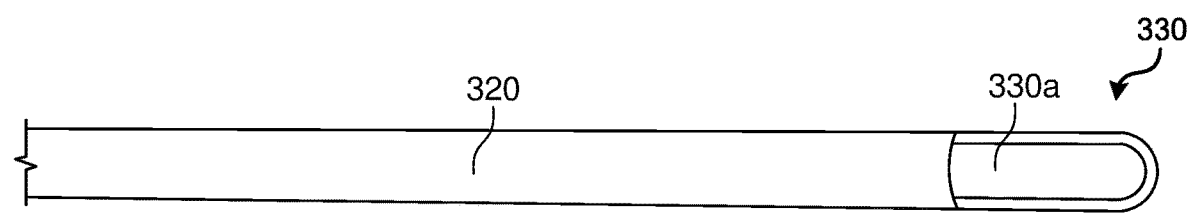
FIG. 4A shows an enlarged view of the cannula and distal end of the microdebrider inner component of the microdebrider apparatus of FIGS. 1A-1B, in accordance with some implementations of the disclosure.
Figure 4B:
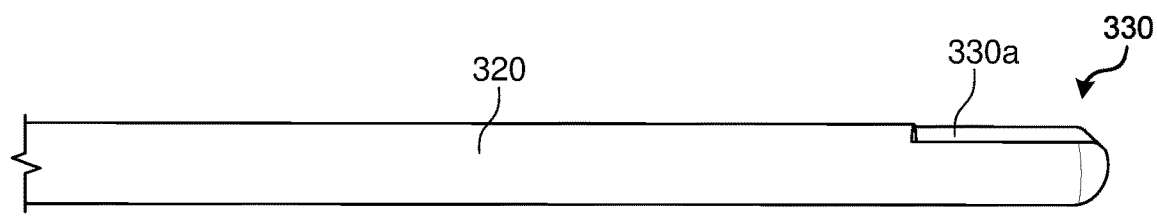
FIG. 4B shows another enlarged view of the cannula and distal end of the microdebrider inner component of the microdebrider apparatus of FIGS. 1A-1B, in accordance with some implementations of the disclosure.
Figure 4C:
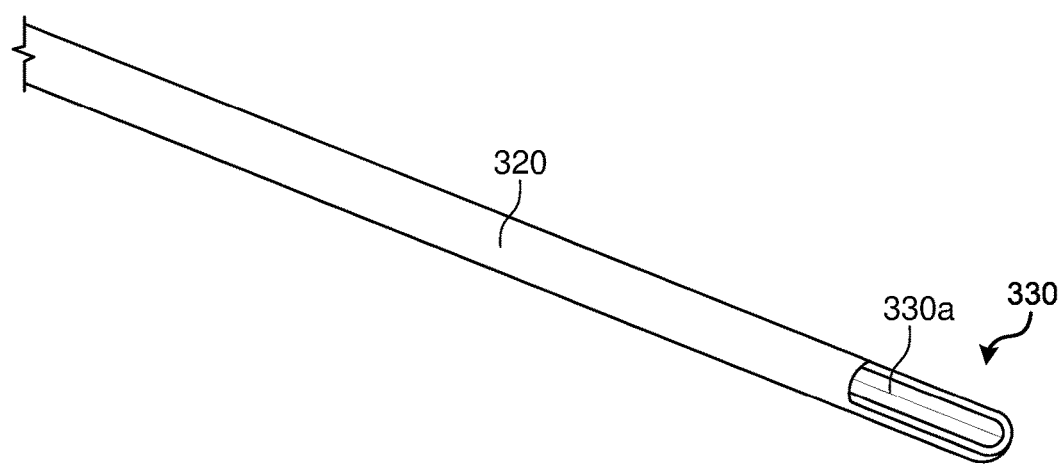
FIG. 4C shows another enlarged view of the cannula and distal end of the microdebrider inner component of the microdebrider apparatus of FIGS. 1A-1B, in accordance with some implementations of the disclosure.

The microdebrider inner component 300 includes a head 310, cannula 320, and distal end or cannula tip 330 that has an opening 330a. FIGS. 4A-4C show different perspective views of the cannula 320 and distal end 330 of inner component 300. A proximal end of head 310 may couple to a suction tool (not shown) via a suction line (not shown) that suctions debrided tissue and/or irrigation fluid at a distal end 330 during operation of apparatus 10. The distal end 330 of cannula 320 may include a rotating instrument (e.g., blade or burr) for performing debriding functions.

During operation, inner component 300 may rotate or oscillate within the outer component 200 to facilitate debriding of tissue by apparatus 10. Multiple options for length of the cannula apparatus 10, diameter of the outer cannula 120, and diameter of the inner cannula/channel 320 are envisioned. Cannula apparatus lengths could range between 5 cm and outer diameters between 2.2 mm and 8 mm, and inner diameters between 2.0 mm and 7.5 mm, respectively.

In this example, apparatus 10 is assembled by moving the microdebrider inner component 300 through the microdebrider outer component 200 (e.g., starting at an opening at a proximal end of head 210 of outer component 200) such that cannula 320 moves through cannula 220, and by moving optical component 100 over cannula 220 (e.g., starting at the distal end of microdebrider outer component 200) such that cannula 120 moves over cannula 220. Manners of assembly in which the integral parts are not detachable or manufactured as one piece are also envisioned, but it should be appreciated that the apparatus 10 incorporates an optical component 100 having a cannula 130 containing a cannula 220 of an outer component 200, which contains a cannula 320 of an inner component 300.

In some implementations, head 210 and head 310 can be implemented as a single housing. In some implementations, head 210 and head 310 can be omitted from outer component 200 and inner component 300, respectively. For example, each of cannula 220 and cannula 320 can couple to (removably or non-removably) to the same proximal housing. In such implementations, optical component 100 could also couple to the same proximal housing.

Figure 5:
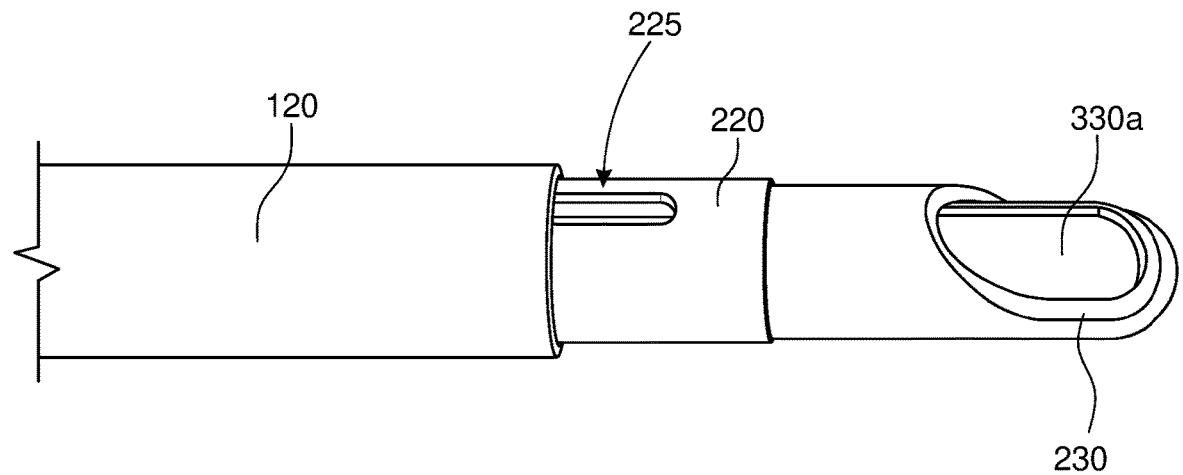
FIG. 5 depicts a distal portion of the assembled microdebrider apparatus of FIG. 1B in a position whereby the microdebrider outer and inner cannulas are rotatably positioned such that a tip of the microdebrider apparatus is open and an opening at a distal end of the inner cannula is exposed.
Figure 6:
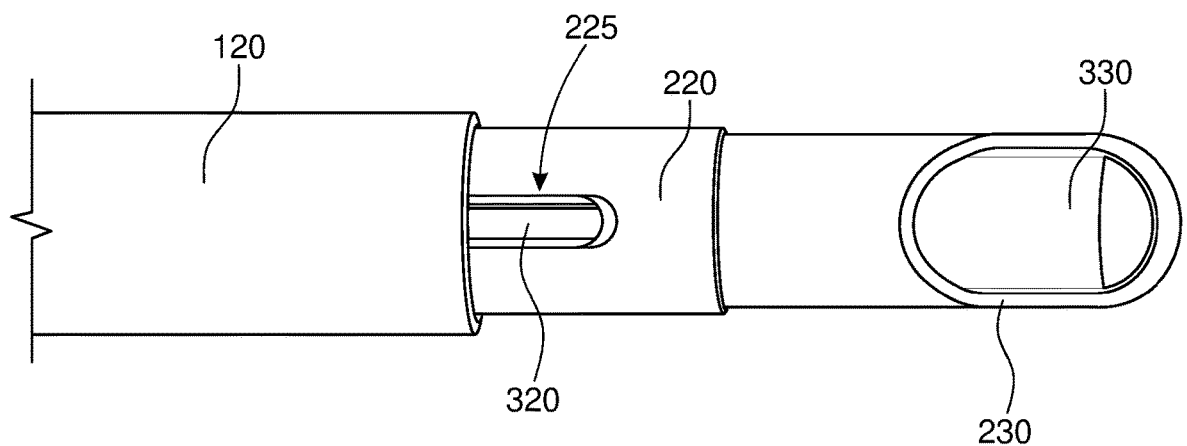
FIG. 6 depicts a distal portion of the assembled microdebrider apparatus of FIG. 1B in another position whereby the microdebrider outer and inner cannulas are rotatably positioned about 180 degrees relative to the position of FIG. 5 such that a tip of the microdebrider apparatus is closed and an opening at a distal end of the inner cannula is not exposed.

FIGS. 5-6 depict the assembled apparatus 10 in two different positions. As depicted, the cannula 120 covers the slot 225 except near the distal end of cannula 220, and the cannula 320 covers the bottom of slot 225, providing a floor for any fluid flowing through the channel between cannula 120 and cannula 220. In FIG. 5, cannulas 220 and 320 are rotatably positioned such that the tip of apparatus 10 is open, and opening 330a of cannula tip 330 is exposed. In FIG. 6, cannula 320 is rotated about 180 degrees relative to the position of FIG. 5, such that the opening 330a is no longer exposed, and the tip of apparatus 10 is closed.

Figure 7:
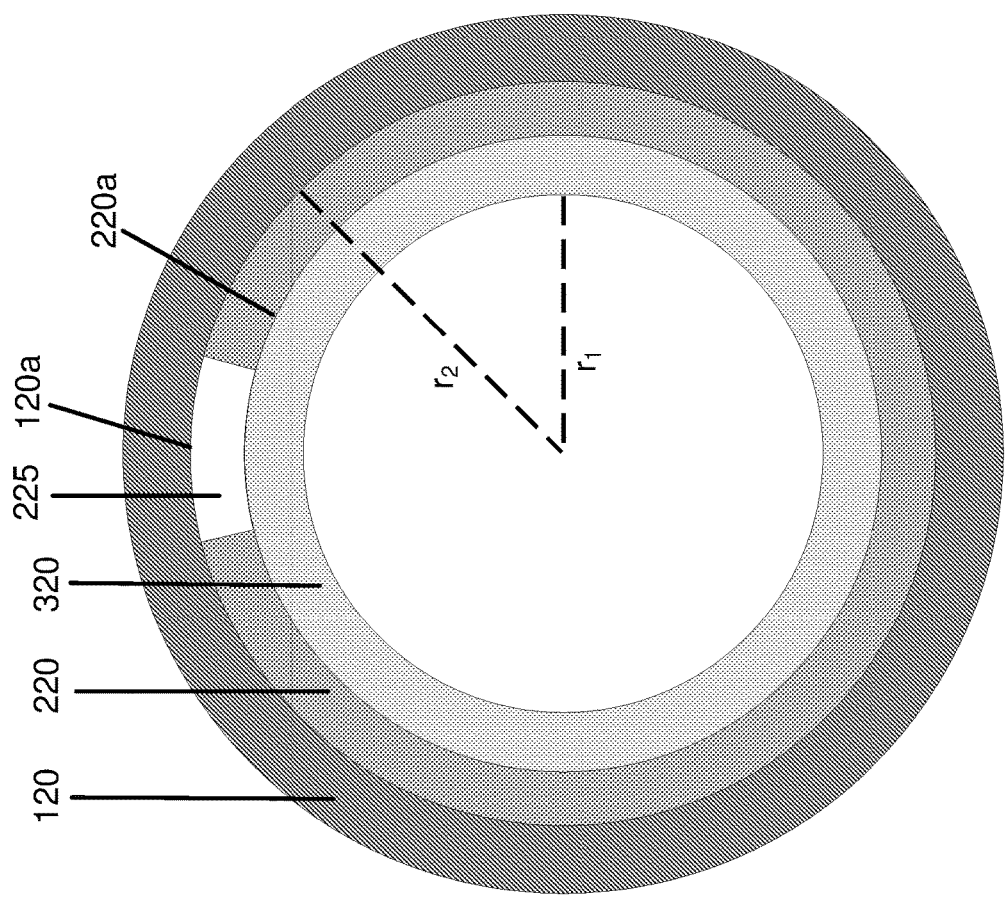
FIG. 7 shows a cross-sectional view of the three cannulas of the microdebrider apparatus of FIG. 1B, in accordance with some implementations of the disclosure.

FIG. 7 depicts a cross-sectional view of the cannulas 120, 220, and 320 of the three components 100-300 after the apparatus 10 is assembled, and will be referenced herein when describing the operation of microdebrider apparatus 10. During use of microdebrider apparatus fluid (e.g., irrigation fluid) is delivered to fluid port 105 via a fluid line (not shown) and into channel 105a of fluid receptacle 110a. The fluid travels, via proximal opening 125a, into an interior of cannula 120. The fluid flows through the space in the slot 225 between cannula 120 and 220 as depicted in FIG. 7. The fluid flows along the longitudinal end of apparatus 10 and flows out the distal end of the combined cannula of apparatus 10 proximal to the distal opening of the cannula 230 and distal to the distal end point of outer cannula 120. The distance between the end point of cannula 120 and amount of exposed irrigation slot 225 could vary between 1 mm and 5 mm.

The foregoing design enables irrigation fluid or other fluid to be delivered through the optical component 100 in a joint space between cannula 120 and cannula 220 in a manner that both maximizes the microdebrider outer diameter (e.g., 2 times $r_2$ in FIG. 7) and minimizes the optical component working channel inner diameter (i.e., the spacing between cannula 120 and 220). By placing at least one slot 225 running longitudinally along the microdebrider cannula 220, fluid can be delivered through the slot 225 to the component tip. As such, by virtue of this design, the customary gap between the inner walls of the working channel of optical component 100 and the outer wall of the microdebrider outer component 200 can be eliminated as depicted in FIG. 7. The fluid may be routed to the end of the component without needing to enlarge the overall space taken up by the component.

In the foregoing arrangement, the outer wall of the cannula 320 of microdebrider inner component 300 may fit flush within the inner wall 220a of the cannula 220 of microdebrider outer component 200. The microdebrider inner component 300 thereby creates a floor to the one or more slots 225 placed into to microdebrider outer component 200. In a similar manner, the inner wall 120a of the working channel of the cannula 120 of optical component 100 provides a roof or ceiling to the slot 225. The slot 225 may therefore confine the irrigation channel to the material thickness of the cannula 220 of outer microdebrider component 200 as well as the width of the slot 225.

Figure 8:
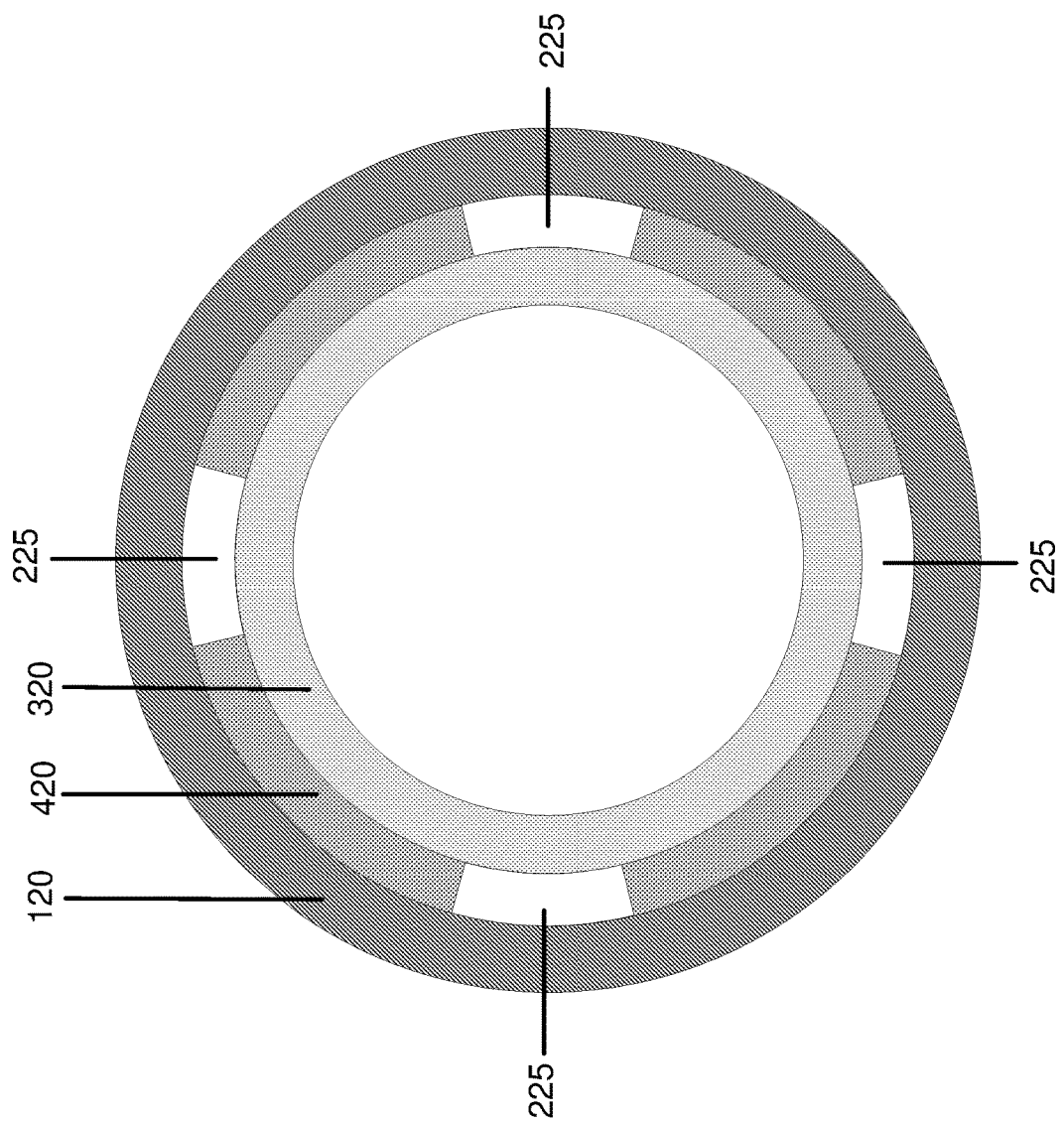
FIG. 8 depicts a cross-sectional view of an example implementation of an assembled microdebrider apparatus having a microdebrider outer component with a cannula having four spaced slots running longitudinally along the cannula, in accordance with some implementations of the disclosure.

In some implementations, multiple slots 225 (e.g., 2, 3, 4, 5, 6, or more) may be spaced circumferentially and running longitudinally along the outer cannula 220. For example, FIG. 8 depicts a cross-sectional view of an example implementation of an assembled microdebrider apparatus having a microdebrider outer component with a cannula 420 having four spaced slots running longitudinally along the outer cannula 220. Having multiple spaced slots 225 may ensure a more uniform delivery and increased volume of fluid at the distal end of the apparatus, often times delivered under pressure.

Figure 9:
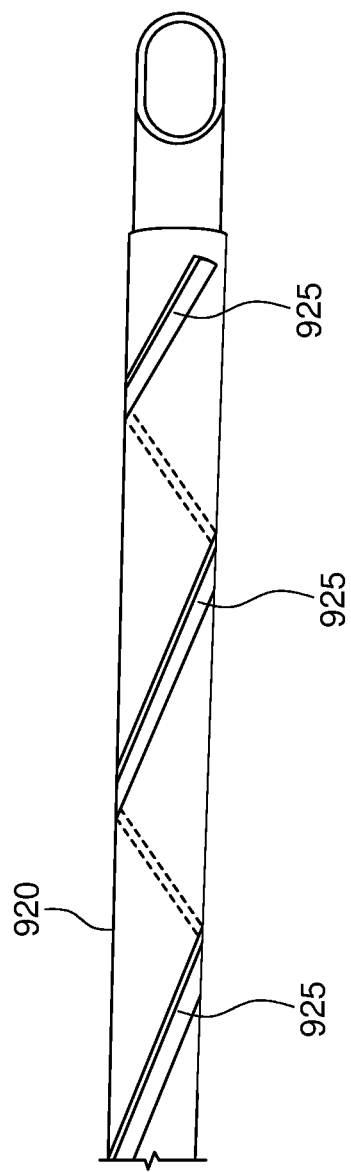
FIG. 9 shows a side view of a cannula of a microdebrider outer component of a microdebrider apparatus, the cannula including a slot that spirals, in accordance with some implementations of the disclosure.

In some implementations, the slots are envisioned to be linear in shape, however in other implementations, the slots may be non-linear in shape and width. Such embodiments may include spiral or mixed horizontal and longitudinal slot configurations. For instance, a spiral slot configuration may allow for tortional closure of the slot in certain applications whereby altering the size and therefore fluid carrying capacity of the slots would be beneficial. By way of example, FIG. 9 shows a side view of a cannula 920 of a microdebrider outer component of a microdebrider apparatus, the cannula 920 including a slot 925 that spirals. In addition to longitudinally extending along the length of cannula 920, slot 925 spirals about the circumference of cannula 920. The dashed lines in FIG. 9 indicate the portion of slot 925 that is not visible from the illustrated side view. Although FIG. 9 shows an example of a cannula 920 having one slot 925 that spirals, in some implementations, the outer cannula can have multiple slots that spiral. In such implementations, the spiraling slots can remain parallel to each other along the longitudinal length of the cannula.

Figure 10:
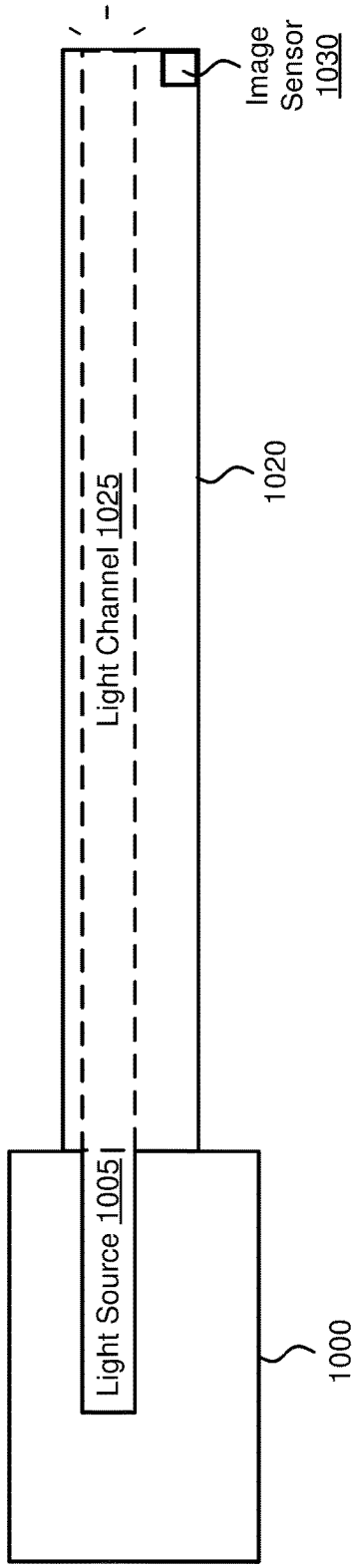
FIG. 10 depicts an example of an optical component comprising a light source and image sensor, in accordance with some implementations of the disclosure.

FIG. 10 depicts an example of an optical component comprising a light source 1005 and image sensor 1030. For ease of illustration, other parts of the optical component (e.g., fluid port and receptacle) are not shown. The example optical component includes a cannula 1020 distally extending from an endoscopic housing 1000. The endoscopic housing 1000 includes a light source 1005 that transmits light that travels through light channel 1025 of cannula 1020, the light channel terminating at a distal end of cannula 1020. The light channel 1025 can be a channel formed in the cannula 1020 (e.g., through a wall of the cannula) separate from a channel (e.g., main cannula opening) via which fluid travels. An image sensor 1030 positioned at a distal end of cannula 1020 collects light reflected from an anatomical structure illuminated by light sensor 1005. The image sensor 1030 itself can also be positioned within the wall of cannula 1020 or in a separate channel attached to the outside of cannula 120. In order to supply power to the light source 1005 and image sensor 1030 to make them operational, the endoscope housing 1000 may provide power to the light source (and the image sensor) via a separate power line or via power-line communications.

Figure 11:
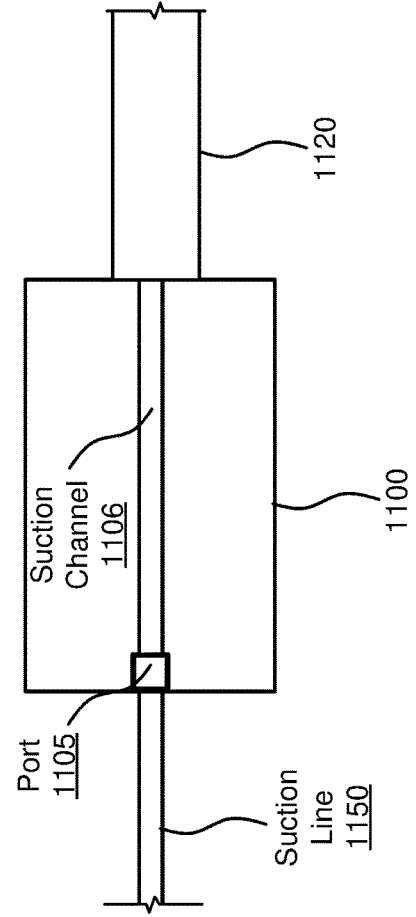
FIG. 11 shows an example of a microdebrider inner component cannula coupled to a housing with a port that couples to a suction line, in accordance with some implementations of the disclosure.

FIG. 11 shows an example of a microdebrider inner component cannula 1120 coupled to a housing 1100. The housing includes a suction channel 1106 to receive debrided tissue and/or irrigation fluid via cannula 1120. The housing also includes a port 1105 that couples to a suction line 1150 (e.g., via suction channel 1106). The suction line 1150 can suction the tissue after debridement. The suction line can also suction the fluid after exiting at the distal end of the microdebrider apparatus. In some implementations, the port 1105 can directly couple to cannula 1120, in which case suction channel 1106 can be omitted.

Cannulas 120, 220, and 320 may be made out of metal and/or rigid or flexible polymer such as PEBA, PEEK or LCP. Disposable and reusable cannulas are also envisioned. In some implementations, the optical cannula shaft 120 may be articulating, flexible, malleable, or otherwise non-linear or curved in configuration. Optical cannula shafts that relay anatomical tip positioning information to an image guidance computer are also envisioned. Inner cannula 220 and 320 may also be flexible and/or articulating thereby allowing them to passively or actively move in relation to an outer flexible or articulating optical cannula.

In some implementations, a powered rotating shafted instrument could be inserted through the second cannula 220 instead of a rotating hollow cannula 320. For example, a shafted burr could be inserted instead of a rotating hollow cannula 320 through the second cannula 220 such that the suction could still occur around the burr tip.

The delivery of irrigation fluid via the cannula and slot configurations described herein are not limited to arthroscopic microdebriders. Similar applications are envisioned for shafted instrumentation passed through an outer cannula in instances whereby slots or indentations/grooves incorporated into the outer diameter of an instrument shaft are required for fluid delivery. It should also be noted that the outer contour of an instrument shaft may be circular or of some other geometric outer contour and that cannulas may also have outer or inner contours that are not necessarily circular in configuration.

FIGS. 12A-14B illustrate example implementations of a single portal surgical apparatus that utilizes instrument shafts configured to extend through an outer cannula (e.g., outer optical cannula 120), and in touching relation with the inner wall of the outer cannula, to divide the inside of the optical cannula into multiple separate fluid channels suitable for irrigation and/or suction operations.

Figure 12C:
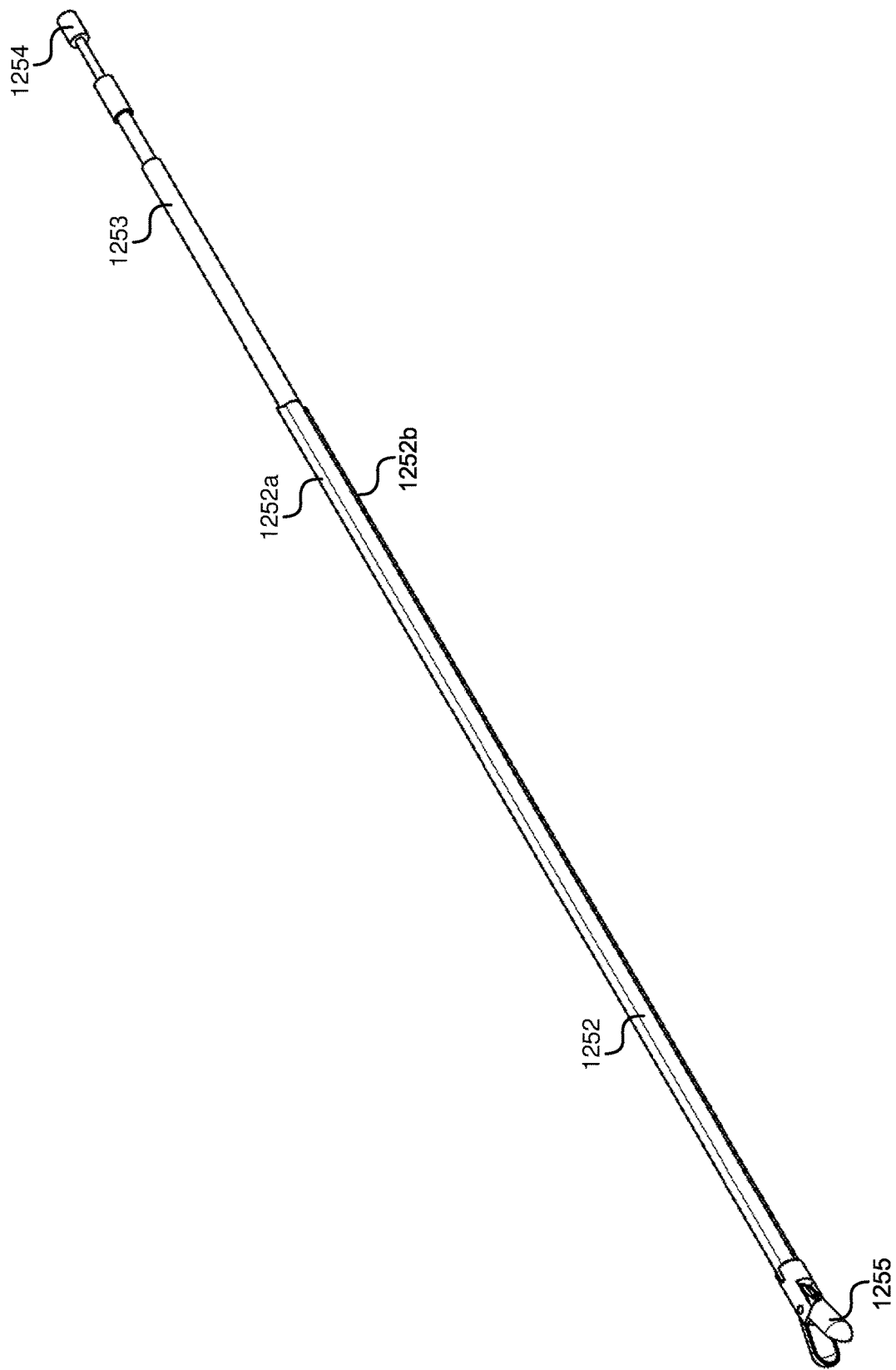
FIG. 12C shows a perspective view of the instrument shaft and distal tool of the single portal surgical apparatus of FIG. 12A.
Figure 12D:
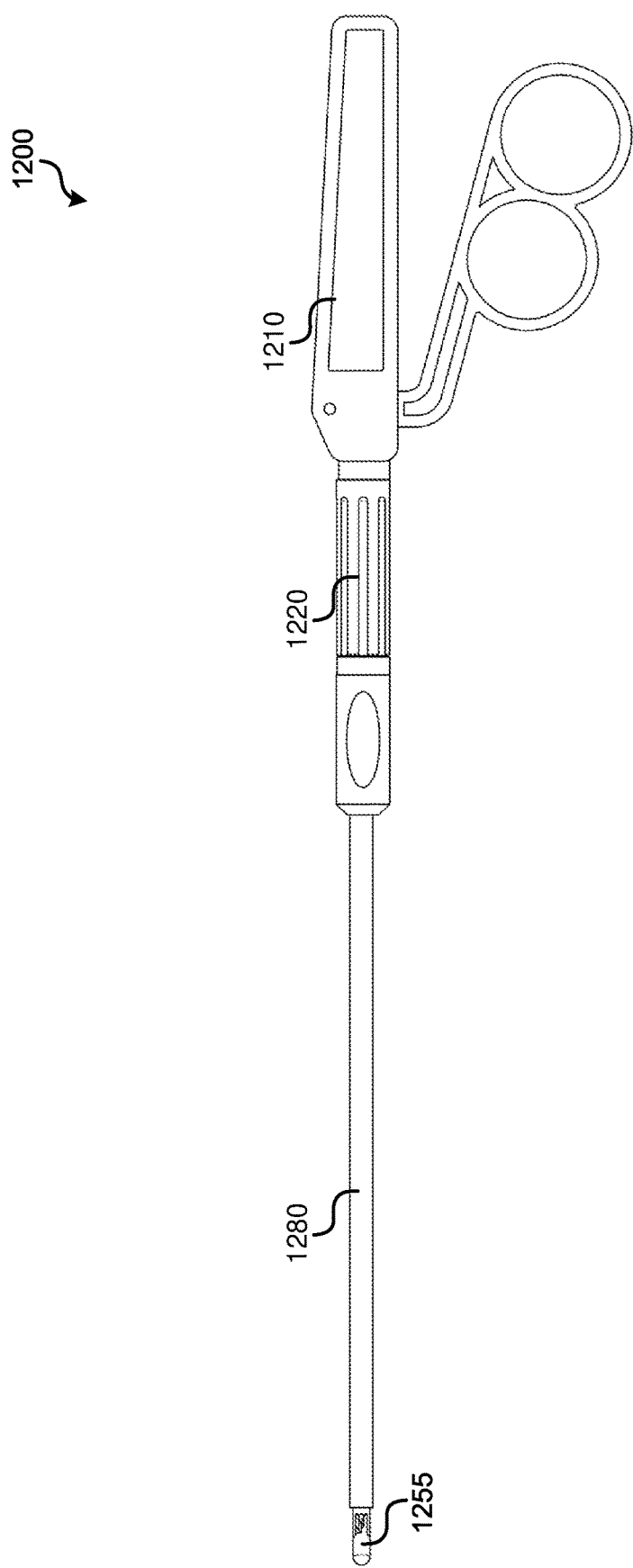
FIG. 12D shows the single portal surgical apparatus of claim 12A after the outer/optical cannula is coupled, and the instrument shaft extends through the outer/optical cannula.

FIGS. 12A and 12D illustrate a single portal surgical apparatus 1200 including a winged instrument shaft 1250 configured to extend through an outer/optical cannula 1280 to divide the inside of the outer/optical cannula into multiple separate fluid channels. The depicted apparatus comprises a handle 1210, a control 1205 that is actuatable to drive a distal tool/tool tip 1255, an instrument shaft with a winged portion 1252, and an instrument shaft connector 1220 distal to handle 1210. The apparatus 1200 can also comprise the outer/optical cannula 1280 that is configured to receive the winged instrument shaft 1250. The outer/optical cannula 1280 can include components similar to the components of the cannulas described above with reference to optical component 100 and/or the optical component of FIG. 10 (e.g., image sensor, light source, fluidic coupling, etc.). FIGS. 12B-12C respectively illustrate side and perspective views of the instrument shaft and distal tool 1255.

The instrument shaft 1250 includes a winged portion 1252 and connector portion 1253 to connect the instrument shaft 1250 to the handle 1210. The connector portion 1253 mechanically couples a proximal end of the instrument shaft 1250 to the instrument shaft connector 1220 distally extending from handle 1210. A housing containing or extending from the instrument shaft connector 1220 can also incorporate irrigation and suction mechanisms that attach to suction and irrigation lines running to apparatus 1200. Connector portion 1253 can be rigid or semi-rigid, and the coupling mechanism of instrument shaft connector 1220 can enable a removable coupling mechanism such as snap fit, press fit, friction fit, magnetic attachment, and/or some other attachment mechanism. One embodiment may include a longitudinal slot in housing 1220 that rotates around shaft connector portion 1253 after 1253 is positioned within the slot (not shown). In alternative implementations, the instrument shaft is integrated and not removable.

Extending proximal to connector portion 1253 is a cable/wire 1254 configured to drive tool tip 1255. The cable/wire 1254 can be configured to run through the instrument shaft 1250 to the tool tip 1255. Instrument handle 1210, housing 1220 and actuating control 1205 can be configured to removably secure instrument shaft segment 1253 in relation to the proximal end of cable wire 1254 so that cable wire 1254, once engaged, can move back and forth within shaft 1252 when engaged and actuated by control 1205. As depicted in this example, the tool tip 1255 includes forceps. However, as further described below, various other instrument tools are envisioned for use with the single portal surgical apparatus 1200, or variants thereof. During operation, control 1205 can be actuated to drive distal tool 1255 via cable 1254. The control 1205 is illustrated as having finger grips that can be grasped to actuate the distal tool 1255. Other controls are envisioned, including, for example, a trigger, a button, a dial, a slide, etc.

The winged portion 1252 of the instrument shaft 1250 includes circumferentially spaced apart wings/structures 1252a and 1252b that protrude from and longitudinally extend along a length of the instrument shaft. When apparatus 1200 is assembled, the shaft 1252 can be inserted through an outer/optical cannula 1280 shown in FIG. 12D such that each of the circumferentially spaced apart wings 1252a and 1252b are in continuous, touching relation with a surface of the inner wall of the outer cannula along a longitudinal length of the inner wall. By virtue of this configuration, the inside of the outer cannula 1280 can be divided into multiple fluid channels that can be configured for suction and/or irrigation functions. A fluid (e.g., a liquid or air/gas) can be transmitted by and/or received by each of the fluid channels. Example implementations of instrument shafts extending through outer cannulas in this manner are illustrated and further described below with reference to FIGS. 13A-13B and FIGS. 14A-14B.

The instrument shaft and outer cannula can be assembled together by inserting a distal end of the instrument shaft 1250 through a proximal end of the outer cannula until the distal end of the instrument shaft 1250 reaches or extends through a distal end of the outer cannula 1280. In such implementations, the instrument shaft 1250 can first couple to the instrument shaft connector 1220 via connector portion 1253, followed by the outer cannula. Alternatively, a proximal end of the instrument shaft 1250 can be inserted or pushed through a distal end of the optical cannula and then coupled to the handle 1210 and/or connector 1220. The latter form of assembly may be preferable in cases where the distal tool is too large to fit through the outer cannula.

Although two circumferentially spaced apart wings/structures 1252a and 1252b are illustrated for dividing the inside of the outer cannula 1280 into two fluid channels, it should be appreciated that additional, circumferentially spaced apart structures can be included to divide the inside of the outer cannula 1280 into more than two fluid channels. Additionally, although the wings 1252a and 1252b are circumferentially spaced apart about 180 degrees along the instrument shaft to enable the formation of two fluid channels that are substantially equal in size, it should be appreciated that other spacing configurations can be implemented, and the formed fluid channels need not be substantially equal in size.

The material properties of winged portion 1252 (and particularly wings 1252a and 1252b), including stiffness, flexibility, malleability, and/or roughness can be selected to enable each wing to continuously remain in contact with a surface of the inner wall along its longitudinal length. The material properties of the inner wall of the outer cannula 1280 can also be taken into consideration when making this selection. For instance, there may me longitudinal or spiral grooves incorporated into the inner surface wall of the cannula to engage the wings thereby securing position and creating a tighter fluid or suction seal.

FIGS. 13A-13B illustrate an example assembly 1300 of a single portal surgical apparatus, the assembly 1300 including an instrument shaft 1320 extending through an outer/optical cannula 1310, and in touching relation with an inner wall of the outer cannula 1310, in accordance with some implementations of the disclosure. FIG. 13A shows a front perspective view, and FIG. 13B shows a front cross-sectional view. As shown, outer surfaces 1320a and 1320b of instrument shaft 1320 are in continuous, touching relation with an inner wall of outer cannula 1310, dividing the inside of the outer cannula 1310 into two separate fluid channels, fluid channel 1335 and fluid channel 1345. In addition, the instrument shaft 1320 is structured to accommodate two separate instruments, a first instrument or cable wire through instrument channel 1322, and a second instrument through instrument channel 1324. The instruments can be removably coupled to or integrated into each respective channel. Various instruments are envisioned for usage, including, for example, forceps, an injection needle, a laser fiber for ablation, suture/suture guides, drills, image guidance probes, etc.

Figure 14A:
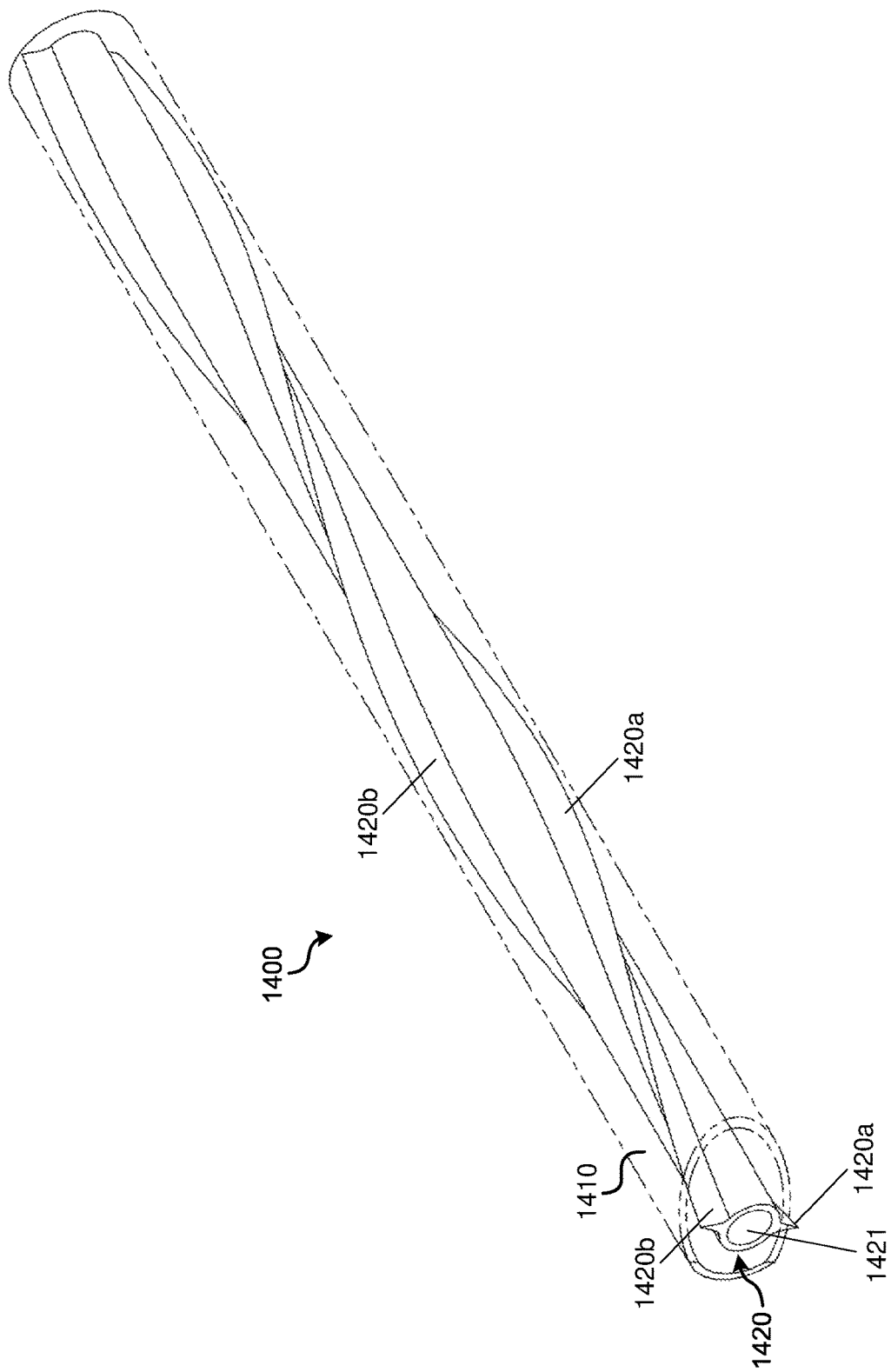
FIG. 14A shows a front perspective view of another assembly of a single portal surgical apparatus, the assembly including an instrument shaft extending through an outer/optical cannula, and in touching relation with an inner wall of the outer cannula, in accordance with some implementations of the disclosure.
Figure 14B:
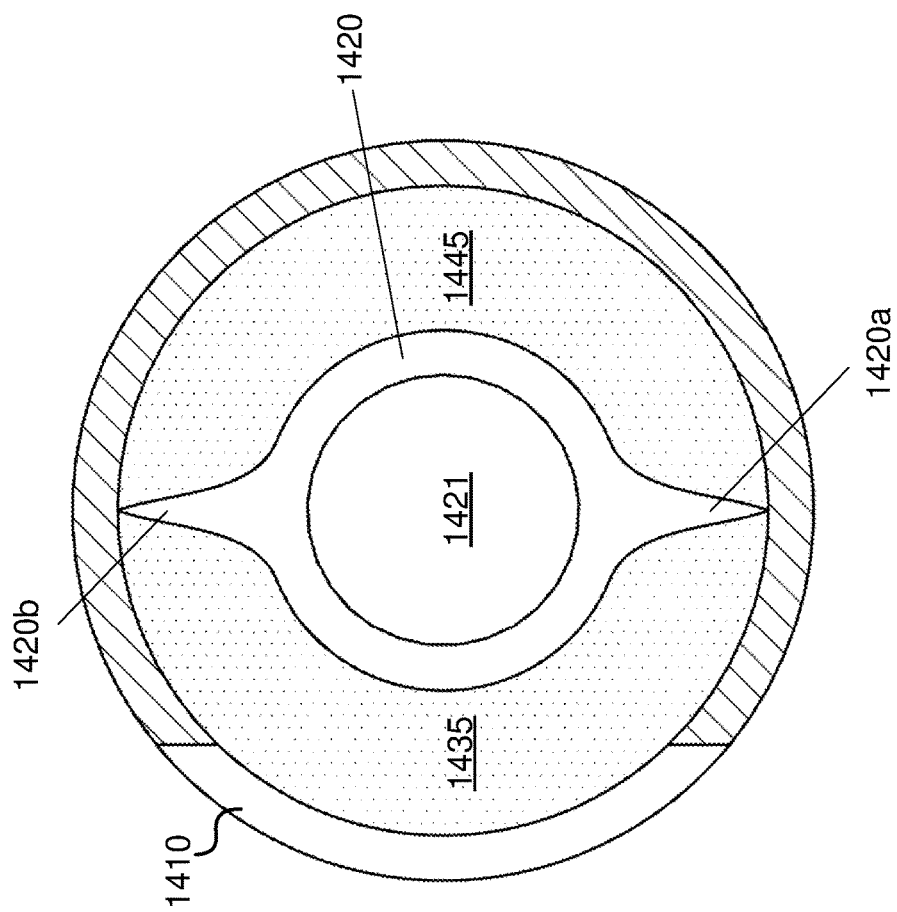
FIG. 14B shows a front cross-sectional view of the assembly of FIG. 14A.

FIGS. 14A-14B illustrate another example assembly 1400 of a single portal surgical apparatus, the assembly 1400 including an instrument shaft 1420 extending through an outer/optical cannula 1410, and in touching relation with an inner wall of the outer cannula 1410, in accordance with some implementations of the disclosure. FIG. 14A shows a front perspective view, and FIG. 14B shows a front cross-sectional view. As shown, circumferentially spaced apart winged structures 1420a and 1420b of instrument shaft 1420 are in continuous, touching relation with an inner wall of outer cannula 1410, dividing the inside of the outer cannula 1410 into two separate fluid channels, fluid channel 1435 and fluid channel 1445. The instrument shaft 1420 is structured to accommodate an instrument through instrument channel 1421. The instrument can be removably coupled to or integrated into the channel 1421. As depicted by FIG. 14A, the winged structures 1420a and 1420b circumferentially spiral about the instrument shaft along its longitudinal length. By virtue of this configuration, the instrument shaft can be better stabilized within the outer cannula 1410. In alternative implementations, the winged structures 1420a and 1420b can linearly run along the longitudinal length.

Although described above in terms of various example implementations and implementations, it should be understood that the various features, aspects and functionality described in one or more of the individual implementations are not limited in their applicability to the particular implementation with which they are described, but instead can be applied, alone or in various combinations, to one or more of the other implementations of the application, whether or not such implementations are described and whether or not such features are presented as being a part of a described implementation. Thus, the breadth and scope of the present application should not be limited by any of the above-described example implementations.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The terms "substantially" and "about" used throughout this disclosure, including the claims, are used to describe and account for small fluctuations, such as due to variations in manufacturing tolerances. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

To the extent applicable, the terms "first," "second," "third," etc. herein are merely employed to show the respective objects described by these terms as separate entities and are not meant to connote a sense of chronological order, unless stated explicitly otherwise herein.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide some instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various implementations set forth herein are described in terms of example block diagrams, flow charts and other illustrations. As will become apparent to one of ordinary skill in the art after reading this document, the illustrated implementations and their various alternatives can be implemented without confinement to the illustrated examples. For example, block diagrams and their accompanying description should not be construed as mandating a particular architecture or configuration.

While various implementations of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present disclosure. Also, a multitude of different constituent module names other than those depicted herein can be applied to the various partitions. Additionally, with regard to flow diagrams, operational descriptions and method claims, the order in which the steps are presented herein shall not mandate that various implementations be implemented to perform the recited functionality in the same order unless the context dictates otherwise.

What is claimed is:

1. An apparatus, comprising:
   a first cannula to couple to a fluid receptacle such that fluid flows from the fluid receptacle through a proximal opening of the first cannula;
   a second cannula to couple within the first cannula such that an outer wall of the second cannula is in touching relation with an inner wall of the first cannula, the second cannula including a first distal opening and a first slot longitudinally extending along a length of the second cannula, wherein the fluid entering the proximal opening of the first cannula is to flow through the first slot and exit at a distal end of the apparatus; and
   a third cannula to couple within the second cannula such that an outer wall of the third cannula is in touching relation with an inner wall of the second cannula, the third cannula including a second distal opening that rotationally interacts with the first distal opening during debridement of tissue,
   wherein:
      the fluid entering the proximal opening of the first cannula is to flow through a channel defined by an opening between a first boundary and a second boundary, the opening including the first slot, the first boundary including a longitudinal portion of the inner wall of the first cannula, and the second boundary including a longitudinal portion of the outer wall of the third cannula,
      a thickness of the channel is substantially the same as a thickness of the second cannula between the outer wall of the second cannula and the inner wall of the second cannula; and
      the outer wall of the third cannula is flush against the inner wall of the second cannula along the channel.

2. The apparatus of claim 1, wherein:
   the second cannula further includes a second slot longitudinally extending along the length of the second cannula; and the fluid entering the proximal opening of the first cannula is to flow through the first slot and the second slot, and exit at the distal end of the apparatus.

3. The apparatus of claim 2, wherein:
the second cannula further includes a third slot longitudinally extending along the length of the second cannula; and
the first slot, second slot, and third slot are circumferentially spaced along the second cannula.

4. The apparatus of claim 1, wherein the first slot is substantially linear along the length of the second cannula.

5. The apparatus of claim 1, wherein the first slot spirals along the length of the second cannula.

6. The apparatus of claim 1, wherein the outer wall of the second cannula is flush against the inner wall of the first cannula along a longitudinal length of the first cannula.

7. The apparatus of claim 1, further comprising: a housing coupled to a proximal end of the third cannula, the housing comprising a port configured to couple to a suction line that suctions the tissue after debridement or the fluid after exiting at the distal end of the apparatus.

8. The apparatus of claim 7, wherein the housing further comprises a suction channel configured to receive the tissue or the fluid via the third cannula.

9. The apparatus of claim 1, wherein an edge of the third cannula along the second distal opening is sharpened.

10. The apparatus of claim 1, further comprising:
a light source to transmit light to a location of the tissue during debridement; and
an image sensor to image the location during debridement.

11. The apparatus of claim 10, wherein the first cannula comprises a channel via which the light transmitted by the light source travels.

12. The apparatus of claim 1, further comprising: the fluid receptacle, wherein the fluid receptacle is configured to fluidically couple to a fluid source, and the fluid receptacle is longitudinally rotatable.

13. The apparatus of claim 1, wherein the third cannula is to removably couple within the second cannula.

14. The apparatus of claim 13, wherein the second cannula is to removably couple within the first cannula.

15. The apparatus of claim 1, wherein the third cannula is integrated within the second cannula.

16. The apparatus of claim 1, wherein a length of the apparatus is between 5 cm and 25 cm, an outer diameter of the first cannula is between 2.2 mm and 8 mm, and an inner diameter of the third cannula is between 2.0 mm and 7.5 mm.

17. The apparatus of claim 1, wherein the apparatus is a single portal microdebrider.

18. The apparatus of claim 17, wherein a distal end of the third cannula comprises a rotating instrument for debriding tissue.

* * * * *